United States Patent [19]
Fukuchi et al.

[11] Patent Number: 5,243,184
[45] Date of Patent: Sep. 7, 1993

[54] MIRROR-FOLLOWING IMAGING METHOD AND DEVICE

[75] Inventors: Hiroyuki Fukuchi; Toru Ishikura, both of Yokohama, Japan

[73] Assignee: Kabushiki Kaisha Kirin Techno System, Yokohama, Japan

[21] Appl. No.: 800,006

[22] Filed: Nov. 29, 1991

[30] Foreign Application Priority Data

Nov. 30, 1990 [JP] Japan ............................. 2-339683

[51] Int. Cl.$^5$ ............................................. G01N 9/04
[52] U.S. Cl. ............................. 250/223 R; 250/223 B; 358/106
[58] Field of Search ........... 250/234, 235, 236, 223 R, 250/223 B, 571, 572; 356/239, 240; 358/101, 107, 108, 106; 209/522, 526

[56] References Cited
U.S. PATENT DOCUMENTS 4,914,289 4/1990 Nguyen et al. ............. 356/240
5,059,031 10/1991 Hamel et al. ............... 250/223 B Primary Examiner—David C. Nelms
Attorney, Agent, or Firm—Jacobson, Price, Holman & Stern

[57] ABSTRACT

A mirror-following imaging method is for reflecting against a rotary mirror lights from an object to be inspected being carried by conveying means to be incident on imaging means so as to make an image of the object in a frame. The mirror-following imaging method comprises the steps of detecting a positional deflection amount of the image of the object in the frame by the imaging means, anticipating a position for the object to be next imaged at, based on the detected positional deflection amount and a conveying speed of the conveying means, and rotating the mirror corresponding to the anticipated position. The mirror-following imaging method enables the object to be inspected to be correctly followed by the mirror.

8 Claims, 4 Drawing Sheets

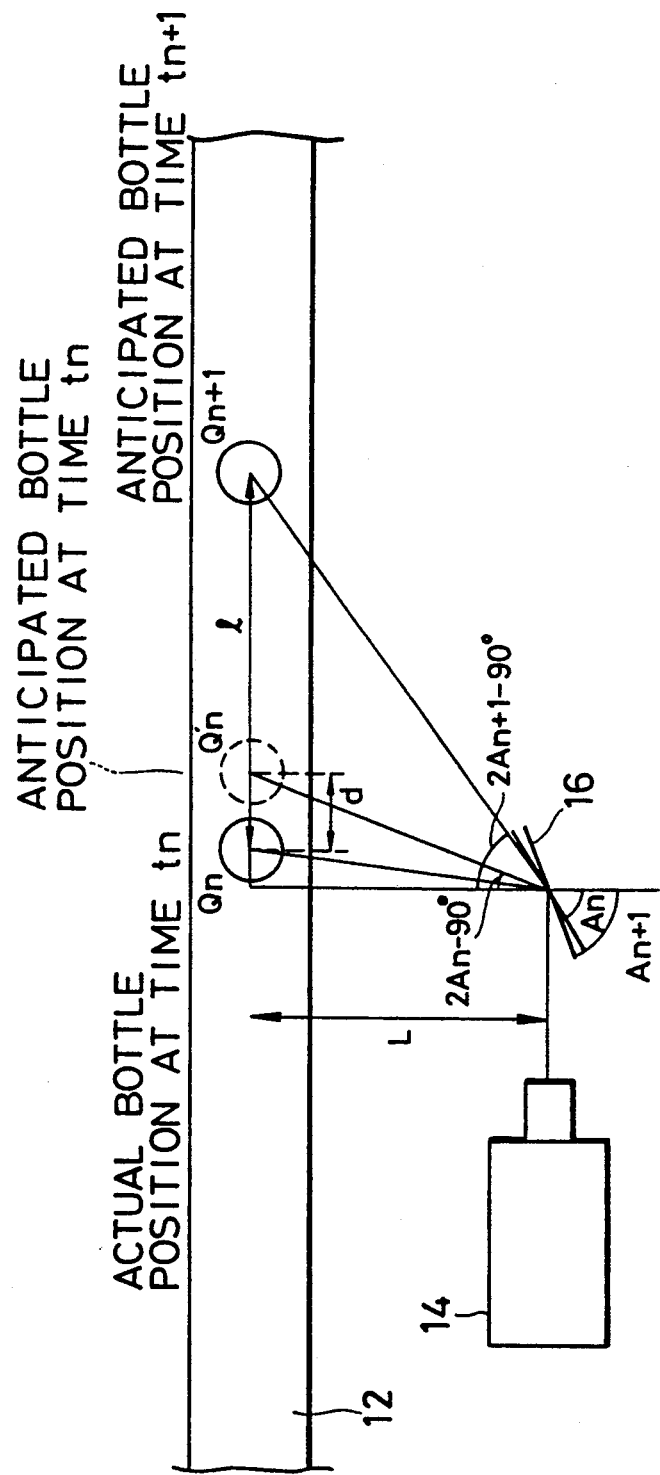

MIRROR-FOLLOWING IMAGING METHOD AND DEVICE

BACKGROUND OF THE INVENTION

The present invention relates to a mirror-following imaging method and device for following an object to be inspected being carried by conveying means to be incident on imaging means so as to image the object in a frame.

It is necessary to inspect for defects glass bottles, as of liquors, beverages, foods, etc., whether they are fresh from glass forming machines or are used. Conventionally, for the inspection of such bottles for defects, a bottle to be inspected is mounted on an inspection table by handling means to be imaged by a mirror rotated synchronously with a motion of the table; the images of the bottle are received by a stationary imaging means; and the inspected bottle is dismounted from the table.

Thus, the conventional inspection needs special bottle tables for the inspection, and special handling means for mounting and dismounting the bottles on and from the tables. As a resultant problem, this adds to the costs.

To solve this problem, it is desirable to inspect such bottles rotated on conveyors by means of, e.g., a belt, without the inspection tables.

But a problem with this desirable inspection of the bottles on conveyors is that because the conveying speed of the bottles and the interval between the bottles change at random, the mirror which is simply rotated synchronously with the conveyor cannot correctly follow motions of the bottles.

SUMMARY OF THE INVENTION

An object of the present invention is to provide a mirror-following imaging method and device which enable objects to be inspected to be followed by a mirror.

This object is achieved by a mirror-following imaging method for reflecting against a rotary mirror lights (radiation) from an object to be inspected being carried by conveying means to be incident on imaging means so as to make an image of the object in a frame, the method comprising the steps of: detecting a positional deflection amount of the image of the object in the frame by the imaging means; anticipating a position for the object to be next imaged at, based on the detected positional deflection amount and a conveying speed of the conveying means; and rotating the mirror corresponding to the anticipated position.

This object is also achieved by a mirror-following imaging device for reflecting against a rotary mirror lights from an object to be inspected being carried by conveying means to be incident on imaging means so as to make an image of the object in a frame, the device comprising: conveying speed detecting means for detecting a conveying speed of the conveying means; positional deflection detecting means for detecting a positional deflection of the image of the object in the frame; mirror rotation angle computing means for anticipating a position for the object to be next imaged at, based on the positional deflection amount detected by the positional deflection detecting means, and the conveying speed detected by the conveying speed detecting means, and computing a rotation angle of the mirror which enables the imaging means to image the object; and, mirror rotating means for rotating the mirror by the rotation angle detected by the mirror rotation angle computing means.

BRIEF DESCRIPTION OF THE DRAWINGS

FIG. 5 is a view explaining the mirror-following imaging method used in the mirror-following imaging device of FIG. 1.

DETAILED DESCRIPTION OF THE INVENTION

The mirror-following imaging device according to one embodiment of the present invention will be explained with reference to FIGS. 1 to 4. This embodiment will be explained by means of the case that the body or sidewall of a bottle is imaged for the inspection of defects.

Figure 1:
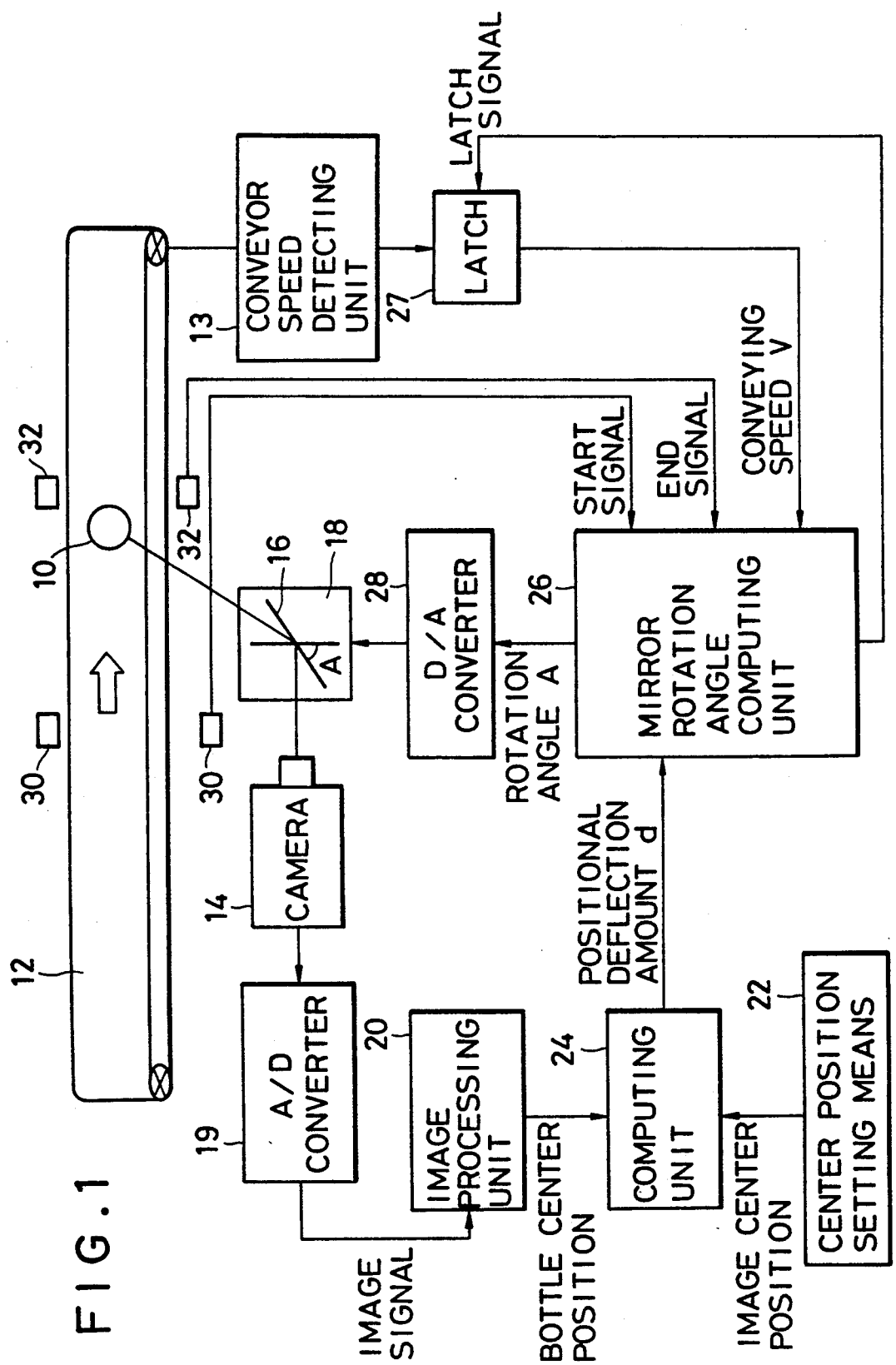
FIG. 1 is a view of the mirror-following imaging device according to one embodiment of the present invention.

FIG. 1 is a block diagram of the mirror-following imaging device according to this embodiment.

A bottle 10 to be inspected is carried on a conveyor 12 from the left to the right as viewed in FIG. 1. The carrying speed V of the conveyor 12 is detected by a conveyor speed detecting unit 13. A mirror 16 is provided for forming an image Q of the bottle 10 by a camera 14. This mirror 16 is freely rotated by mirror driving means 18.

An analog image signal from the camera 14 is converted into a digital image signal by an A/D converter 19 to be supplied to an image processing unit 20.

The image processing unit 20 inspects the body or sidewall of the bottle 10 for defects, based on an image Q of the bottle 10 which has been taken in a frame P by the camera 14, and detects the center position of the image Q of the bottle 10 in the frame P, based on the contour of the image Q. The width h of the image Q of the whole bottle 10 has been beforehand inputted in the image processing unit 20.

Figure 2:
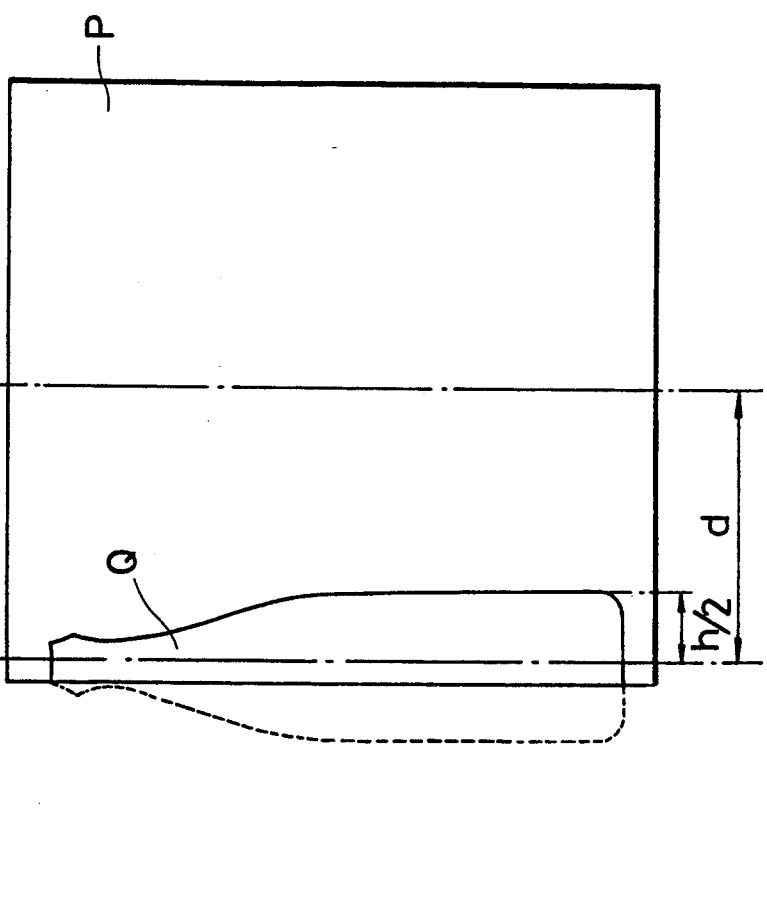
FIG. 2 is a view of an imaged frame of the mirror-following imaging device of FIG. 1.
Figure 3:
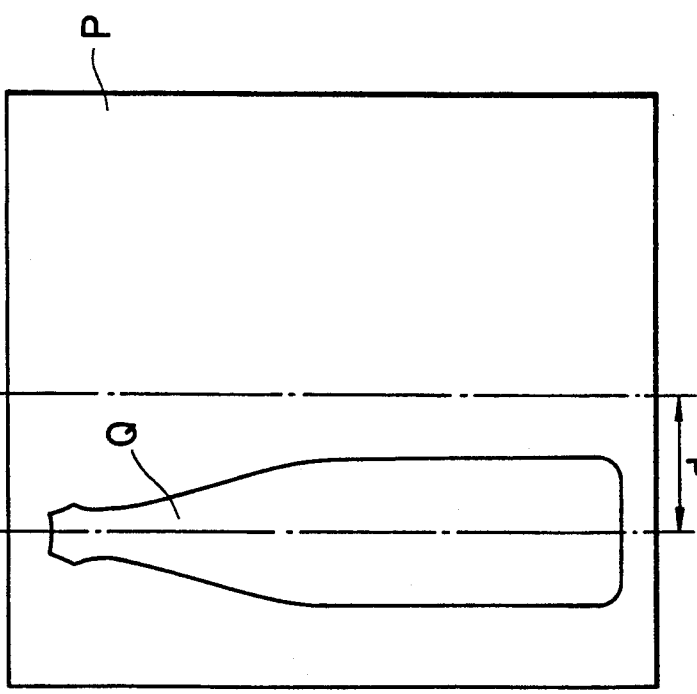
FIG. 3 is a view of an imaged frame of the mirror-following imaging device of FIG. 1.

In the case, as shown in FIG. 2, that the image Q in the frame P is of the whole bottle 10, the center position of the bottle 10 is detected based on the contours of both sides of the image Q. In the case, as shown in FIG. 3, that the image Q in the frame P is of only one side of the bottle 10, the center position of the bottle 10 is anticipated based on the contour of the imaged side of bottle 10 and the width h of the image Q, which has been beforehand inputted in the image processing unit 20.

The center position of the frame P is preset by frame center position setting means 22. A computing unit 24 computes a center position deflection amount, based on the center position of the image Q of the bottle 10 detected by the image processing unit 20 and the center position preset by the frame center position setting means 22, converts the frame center position deflection amount into an actual distant deflection amount d on the conveyor 12, and outputs the amount d to a mirror rotation angle computing unit 26.

The mirror rotation angle computing unit 26 anticipates a position where the bottle 10 will be next imaged, based on the image center position deflection amount d of the bottle 10 from the image processing unit 20 and a conveying speed V from the conveyor speed detecting unit 13, and computes a mirror rotation angle A which will enable the bottle 10 to be imaged at the anticipated position. The conveying speed V from the conveyor speed detecting unit 13 is latched by a latch 27 in response to a latch signal from the mirror rotation angle computing unit 26.

A digital rotation angle A is converted to an analog rotation angle A to be outputted to a mirror driving device 18.

The mirror driving device 18 drives the mirror 16 to rotate by a rotation angle A supplied by the mirror rotation angle computing unit 26, whereby the bottle 10 being carried on the conveyor 12 can be imaged by the camera 14.

On the conveyor 12 there are provided sensors 30, 32 for determining a range for the mirror 16 to follow the bottle 10. When the sensor 30 on the left side as viewed in FIG. 1 detects the passage of the bottle 10, the mirror 16 begins to follow the bottle 10, and when the sensor 32 on the right side as viewed in FIG. 1 detects the passage of the bottle 10, the mirror 16 stops following the bottle 10 and is ready to follow a next bottle 10 on the conveyor.

The method for computing a rotation angle A by the mirror rotation angle computing unit 26 will be explained below in good details with reference to FIGS. 4 and 5.

Figure 4:
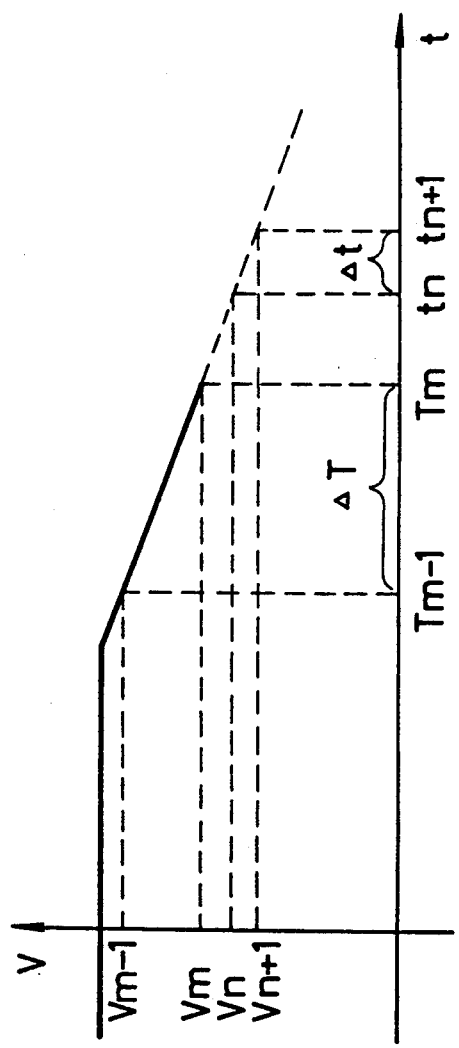
FIG. 4 is a view explaining the mirror-following imaging method used in the mirror-following imaging device of FIG. 1.

FIG. 4 is a graph of changes of a conveying speed V of the conveyor 12 with respect to time. To anticipate a conveying speed V of the conveyor 12, a conveying speed V is sampled at a sampling time interval $\Delta T$. In this anticipation, a time of a preceding sampling is represented by Tm; a conveying speed at this time, Vm; a time of a sampling preceding but one, Tm−1; and a conveying speed at this time, Vm−1, and the conveying speed is assumed to change linearly. A conveying speed Vn at a time tn at which a current image has been taken is as follows.

$$Vn = Vm + (Vm - Vm-1) \times (tn - Tm)/\Delta T. \quad (1)$$

A conveying speed Vn+1 at a time tn+1 at which a next image is to be taken after a time interval $\Delta t$ is $$Vn+1 = Vm + (Vm - Vm-1) \times (tn+1 - Tm)/\Delta T \quad (2)$$

$\Delta t$ ($=tn+1-tn$) is a time interval at which the bottle 10 is imaged by the camera 14. In this embodiment $\Delta t = 16.6$ msec.

FIG. 5 is a view explaining the method for computing an anticipated position of the bottle 10. In FIG. 5, Qn' represents anticipated position of the bottle 10 at a time tn; Qn, an actual position of the bottle 10 at a time tn; and Qn+1, an anticipated position of the bottle 10 at a time tn+1. FIG. 5 shows the case an actual position of the bottle 10 is behind an anticipated position Qn' at a time tn.

When a distance over which the bottle 10 is carried from a time tn to a time tn+1 is represented by l, a deflection amount between an anticipated position Qn' of the bottle 10 and an actual position Qn of the bottle 10 at a time tn, d (d is positive when an actual position Qn is ahead of an anticipated position Qn', for example, in FIG. 5, d is negative); a rotation angle of the mirror 16 at a time tn, An; and a rotation angle of the mirror 16 at a time tn+1, An+1, the following relationship holds.

$$l = \Delta t (Vn + Vn+1)/2 \quad (3)$$

$$l + d = L\{\tan(2An+1-90°) - \tan(2An-90°)\} \quad (4)$$

where L represents a distance from the rotary shaft of the mirror 16 to the center position of the conveyor 12.

Based on Formulas (3) and (4), and Formulas (1) and (2) for giving Vn and Vn+1, a rotation angle An+1 at a time tn+1 can be given as follows.

$$An+1 = \tfrac{1}{2} \times \tan^{-1}\{(L \tan(2An))/(L - K \tan(2An))\}$$

$$K = (\Delta t/\Delta T) \times (Vm - Vm-1) \times (tn - Tm + \tfrac{1}{2}\Delta T) + \Delta t \cdot Vm + d \quad (5)$$

where $An+1 = 45°$ when $An = \tfrac{1}{2} \times \tan^{-1}\{L/(l+d)\}$.

Thus, conveying speeds Vn and Vn+1 at times tn and tn-1 are anticipated based on times tm−1, Tm in view of a deflection amount d between an anticipated position Qn' of the bottle 10 and an actual position Qn thereof, whereby a position Qn+1 of the bottle at a time tn+1 can be anticipated. The rotation angle An of the mirror 16 is controlled so as to be An+1 which enables the bottle 10 to be imaged at the anticipated position Qn+1. Resultantly the bottle 10 can be imaged by the camera 14 constantly at a position near the center of a frame P, and even when a conveying speed of the conveyor 12 changes, or the conveying state of the bottle 10 changes at random, the camera 16 can correctly follow the bottle 10 being carried and image the bottle 10.

In this embodiment the conveying speed of the conveyor 12 is anticipated based on a preceding change of a conveying speed, and based on an anticipated conveying speed, a position of the bottle where the bottle is to be imaged is anticipated. But a next imaging position of the bottle 10 may be anticipated on the assumption that a conveying speed V of the conveyor 12 is kept constant while the mirror is following the bottle 10.

When it is assumed that a conveying speed Vn at a time tn is maintained from the time tn to a time tn+1, the following formulas hold.

$$l = \Delta t \times Vn$$

$$l + d = L\{\tan(2An+1-90°) - \tan(2An-90°)\}.$$

Based on these formulas, a rotation angle An+1 at a time tn+1 is given as follows.

$$An+1 = \tfrac{1}{2} \times \tan^{-1}\{(L \tan(2An))/(L - (\Delta t Vn + d)\tan(2An))\}$$

Where $An+1 = 45°$ when $An = \tfrac{1}{2} \times \tan^{-1}\{L/(l+d)\}$.

Thus, assuming that a conveying speed Vn of the conveyor 12 is constant and also in view of a deflection amount d between an anticipated position Qn' and an actual position Qn, a position Qn+1 of the bottle 10 at a time tn+1 can be anticipated. The rotation angle An of the mirror 16 is controlled so as to be An+1 which enables the bottle 10 to be imaged by the camera 14 at the anticipated position Qn+1. Resultantly the bottle 10 can be imaged by the camera 14 constantly at a position near the center of the frame P. Even when the conveying state of the bottle 10 is changed at random, the camera 14 can follow the bottle 10 being carried and image the bottle 10.

The present invention is not limited to the above-described embodiment and includes various modifications.

The above-described embodiment has been explained with reference to a case that bottles are imaged, but the present invention is applicable to cases that objects to be detected other than bottles are carried by conveying means.

What is claimed is:

1. A mirror-following imaging method for reflecting against a rotary mirror radiation from an object to be inspected being carried by conveying means to be incident on imaging means so as to make an image of the object in a frame, the method comprising the steps of:

detecting a positional deflection amount of the image of the object in the frame by the imaging means;
   anticipating a position at which the next object is to be imaged, based on the detected positional deflection amount and a conveying speed of the conveying means; and
   rotating the mirror corresponding to the anticipated position.

2. A mirror-following imaging method according to claim 1, wherein, when a rotation angle An of the mirror is $An \neq \frac{1}{2} \times \tan^{-1}\{L/(1+d)\}$, a rotation angle $An+1$ at a time $tn+1$ after a time interval $\Delta t$ from a time $tn$, where $tn$ represents times when an image of an object is to be taken, is given as follows:

$$An+1 = \frac{1}{2} \times \tan^{-1}\{(L \tan(2An))/(L-(\Delta t Vn + d)\tan(2An))\}$$

1 being a distance over which the object is carried from a time tn to a time tn+1,
   d being a deflection amount between an anticipated position Qn' of the object and an actual position Qn of the object at a time tn, and
   L being a distance from a rotary shaft of the mirror to a center position of the conveyor, and wherein $An+1 = 45°$ when $A = \frac{1}{2} \times \tan^{-1}\{L/(1+d)\}$.

3. A mirror-following imaging method according to claim 1, and further comprising the step of continuously detecting the conveying speed of the conveying means at a sampling frequency;

wherein based on a conveying speed of the conveying means at a sample which is prior to a current sample, a conveying speed at a next time an image is taken of the object by the imaging means is anticipated, and, based on this anticipated conveying speed and said positional deflection amount of the image, a position at which the next object is to be imaged is anticipated.

4. A mirror-following imaging method according to claim 3, wherein, when a rotation angle An of the mirror is An $\neq \frac{1}{2} \times \tan^{-1}\{L/(1+d)\}$, with a conveying speed at a time Tm represented by Vm, and a conveying speed at a time tm−1 at a time interval $\Delta T$ before a time Tm represented by Vm−1, where Tm (m=positive integers) represents times at which the conveying speed of the conveyor means is sampled, Vm represents the conveying speeds of the conveyor at times Tm, a rotation angle An+1 at a time tn+1 at a time interval $\Delta t$ after a time tn, where tn (n=positive intergers) represents times when an image of an object is taken by the imaging means, is given as follows $$An+1 = \frac{1}{2} \times \tan^{-1}\{L \tan(2An))/(L - K \tan(2An))\}$$

$$K = (\Delta t/\Delta T) \times (Vm - vm - 1) \times (tn - Tm + \frac{1}{2}\Delta T) + \Delta t \cdot Vm + d$$

1 being a distance over which the bottle is carried from a time tn to a time tn+1,
   d being a deflection amount between an anticipated position Qn' of the bottle at a time tn and an actual position Qn of the bottle, and
   L being a distance from a rotatory shaft of the mirror to a center position of the conveyor, and wherein
   $An+1 = 45°$ when $A = \frac{1}{2} \times \tan^{-1}\{L/(1+d)\}$.

5. A mirror-following imaging device for reflecting against a rotary mirror radiation from an object to be inspected being carried by conveying means to be incident on imaging means so as to make an image of the object in a frame, the device comprising:

conveying speed detecting means for detecting a conveying speed of the conveying means;
   positional deflection detecting means for detecting a positional deflection of the image of the object in the frame;
   mirror rotation angle computing means for anticipating a position at which the next object is to be imaged, based on the positional deflection amount detected by the positional deflection detecting means, and the conveying speed detected by the conveying speed detecting means, and computing a rotation angle of the mirror which enables the imaging means to image the object; and,
   mirror rotating means for rotating the mirror by the rotation angle detected by the mirror rotation angle computing means.

6. A mirror-following imaging device according to claim 5, wherein the mirror rotation angle computing means anticipates a conveying speed at a time of next imaging the object, based on a conveying speed of the conveying means at a time which is before by a period of time, and anticipates a position for the object to be next imaged at.

7. A mirror-following imaging device according to claim 5, further comprising:

a first sensor disposed at a first position of the conveying means for detecting a passage of the object to be inspected; and
   a second sensor disposed at a second position of the conveying means for detecting a passage of the object,
   the mirror starting an operation of following the object to be inspected in response to a detection signal of the first sensor, and finishing the operation in response to a detection signal of the second sensor.

8. A mirror-following imaging device according to claim 6, further comprising:

a first sensor disposed at a first position of the conveying means for detecting a passage of the object to be inspected; and
   a second sensor disposed at a second position of the conveying means for detecting a passage of the object,
   the mirror starting an operation of following the object to be inspected in response to a detection signal of the first sensor, and finishing the operation in response to a detection signal of the second sensor.

* * * * *